United States Patent
Slaker et al.

(10) Patent No.: US 6,719,775 B2
(45) Date of Patent: Apr. 13, 2004

(54) PERCUTANEOUS ENDARTERECTOMY

(75) Inventors: Bradley Slaker, Greenfield, MN (US); Daniel M. Lafontaine, Plymouth, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 390 days.

(21) Appl. No.: 09/766,938

(22) Filed: Jan. 22, 2001

(65) Prior Publication Data

US 2002/0099396 A1 Jul. 25, 2002

(51) Int. Cl.$^7$ ............................................... A61M 29/02
(52) U.S. Cl. ....................................................... 606/194
(58) Field of Search ................................. 606/114, 127, 606/159, 200, 194; 128/898; 600/207; 604/96.01, 101.01, 101.05, 101.02, 104, 133

(56) References Cited

U.S. PATENT DOCUMENTS

| | | | |
|---|---|---|---|
| 4,271,839 A | * 6/1981 | Fogarty et al. | 606/194 |
| 4,321,915 A | 3/1982 | Leighton | 128/4 |
| 4,469,100 A | 9/1984 | Hardwick | |
| 4,479,497 A | 10/1984 | Fogarty et al. | |
| 5,163,927 A | 11/1992 | Woker et al. | 604/271 |
| 5,171,305 A | 12/1992 | Schickling et al. | 604/271 |
| 5,364,345 A | 11/1994 | Lowery et al. | 604/49 |
| 5,472,419 A | 12/1995 | Bacich | 604/55 |
| 6,077,289 A | 6/2000 | Mollenauer | |

FOREIGN PATENT DOCUMENTS

| | | |
|---|---|---|
| DE | 28 47 633 A1 | 11/1978 |
| WO | WO 94/16633 | 1/1994 |

* cited by examiner

Primary Examiner—Danny Worrell
(74) Attorney, Agent, or Firm—Crompton, Seager & Tufte LLC

(57) ABSTRACT

Methods and devices for separating plaque from vessel walls using everting membranes. Everting tubes disposed on catheters are used in one embodiment of the invention to separate plaque from blood vessel walls. One embodiment of the invention utilizes a single everting membrane including a fixed portion, a leading edge, and an advancing portion. The everting tube can have an interior which can be pressurized to propel the everting tube distal edge distally onward, so as to separate the plaque from the vessel inner wall. One device has double everting membranes fixedly attached to a tubular member and having facing advancing membrane portions which may be proximally fixed relative to one another, but are preferably both free to travel distally. The outermost tube can be laid down over the vessel inner wall and the innermost tube laid down over the plaque, with the advancing surfaces of each everting membrane facing each other. Fluid can be supplied under pressure to fill the interior of the everting tubes and thereby distally advance the tube leading edges. The present invention may be used in conjunction with distal emboli capturing filter or distal occlusion devices.

11 Claims, 6 Drawing Sheets

PERCUTANEOUS ENDARTERECTOMY

FIELD OF THE INVENTION

The present invention is related generally to medical devices. More specifically, the present invention includes intravascular devices and catheters for performing endarterectomy.

BACKGROUND OF THE INVENTION

Arteriosclerosis is a common vascular disease in which blood vessels become hardened and blocked or partially blocked by plaque that can substantially reduce blood flow. The accumulation of plaque is often a major factor in the occurrence of myocardial infarction, stroke, and high blood pressure.

To treat arteriosclerosis, minimally invasive techniques have been developed. One minimally invasive technique utilizes percutaneous transluminal coronary angioplasty (PTCA) which can include expanding a balloon under pressure within a coronary artery, and dilating a narrowed area of that artery. While PTCA procedures can significantly dilate narrowed coronary arteries, the treated vessel region may become narrow again in a process known as restenosis. In a substantial percentage of PTCA procedures, the dilated vessel region becomes restenosed.

Another example of a minimally invasive technique is atherectomy. In an atherectomy procedure, a guide catheter can be inserted into the patient's femoral artery and advanced until the distal end of the guide catheter is disposed near the patient's ostium or coronary artery. A guidewire can be inserted into the guide catheter and further advanced into the coronary artery, distally past the occluded region. A therapeutic atherectomy catheter having an atherectomy burr may be advanced over the guidewire, through the guide catheter, and to the narrowed region. The atherectomy burr can be rotated at high speed, causing the plaque to be removed in small particles as the plaque is abraded by the atherectomy burr.

Endarterectomy techniques have been utilized in open chest surgeries. In the endarterectomy technique, an artery may be slit longitudinally along its length by a surgeon, commonly after clamping opposite ends of the exposed vessel. The surgeon may strip the internal plaque away from the vessel walls, and remove the plaque from the vessel through the slit. A significant cleaning procedure typically follows the removal procedure to increase the chance of success. In a high percentage of cases, the vessel thus treated may remain potent for a long time period, rather than rapidly becoming restenosed.

What would be desirable are endarterectomy techniques and devices for performing endarterectomy intravascularly. In particular, what would be advantageous are techniques for performing intravascular endarterectomy using a distant entry site, such as a radial artery entry near the groin.

SUMMARY OF THE INVENTION

The present invention includes methods and devices for removing plaque and separating plaque from blood vessels using everting membranes. In one method according to the present invention, an everting membrane is provided and distally advanced through a vessel having a plaque deposit along the vessel wall. The everting membrane may be considered to have a distally advancing portion, a distally leading edge, and a non-advancing portion, where the advancing portion is distally advanced into the vessel. As the advancing portion is distally advanced into the vessel, the leading edge is distally advancing into the vessel as well. As the advancing membrane portion and leading edge are advanced into the vessel along the vessel inner wall, the everting membrane advances between the plaque and the vessel inner wall, thereby separating the plaque from the inner wall. The non-advancing portion can be effectively laid down over either the vessel inner wall or plaque outer walls, depending on orientation. After separation, the separated plaque may be removed from the vessel.

One device according to the present invention has a tubular member having a single everting membrane, the membrane having an interior in fluid communication with a fluid source. The fluid may be supplied through a fluid lumen, thereby supplying the everting membrane interior with fluid under pressure. The pressurized fluid may then cause the everting membrane to travel distally. The distally traveling membrane leading edge may be used to separate the plaque from the vessel inner wall. In one embodiment of the invention, the everting membrane has a more proximal section slidably and sealingly disposed along the tubular member inner wall.

One double everting membrane device according to the present invention includes an inner tube and an outer tube, with the inner tube having an inner fold and the outer tube having an outer fold. The inner and outer folds may be joined and/or simply travel together at a more proximal location. The inner and/or outer folds preferably have interior portions which may be provided with fluid under pressure, thereby causing the inner and outer folds to travel distally. The inner and outer folds may be considered to have facing advancing portions, leading edge distally advancing portions, and relatively non-advancing portions which will unfold and be laid down against the vessel inner wall and the outer wall of the newly separated plaque. The pair of everting membranes may thus be deployed to separate the plaque from the inner wall. After separation, the everted membranes having the plaque disposed within the inner fold may be removed from the formerly constricted vessel site.

Everting membranes in some methods according to the present invention may be used in conjunction with more distally positioned emboli filters. The deployed emboli filters may provide additional assurance of optimal results during the treatment. In one method, the emboli filter and percutaneous endarterectomy catheter are advanced over a guidewire positioned within the coronary artery from a femoral groin entry site. The present invention allows the stripping or removal of plaque from within coronary and other arteries using an intravascular device, not requiring open chest surgery.

DETAILED DESCRIPTION OF THE INVENTION

Figure 1:
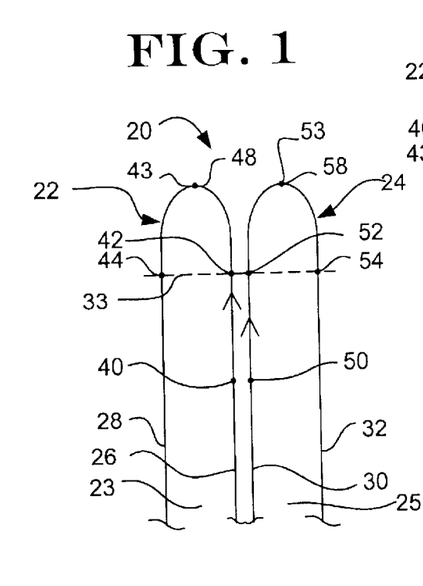
FIG. 1 is a highly diagrammatic, longitudinal, cross-sectional view of a pair of everting membranes in a first, proximal position.

FIG. 1 is a simplified diagram of one membrane pair of an everting membrane device 20 including an outer membrane fold 22 and an inner membrane fold 24. Inner fold 22 and outer fold 24 are disposed relative to a reference line 33, illustrated as a dashed line. Outer fold 22 includes generally a distally advancing portion 26, a distally leading edge portion 48, and a relatively non-advancing portion 28. Outer fold 22 also includes generally an interior region 23. Inner fold 24 includes generally a distally advancing portion 30, a distally leading edge portion 58, and a relatively non-advancing portion 32. Inner fold 24 also includes generally an interior region 25.

Several marker points have been artificially displayed on outer fold 22 and inner fold 24 to illustrate the everting membrane movement. Inner fold 24 has a first marker 50, a second marker 52, a third marker 53, and a fourth marker 54. Similarly, outer fold 22 has a first marker 40, a second marker 42, a third marker 43, and a fourth marker 44. The relative movements of the marker points may be seen in FIG. 2.

Figure 2:
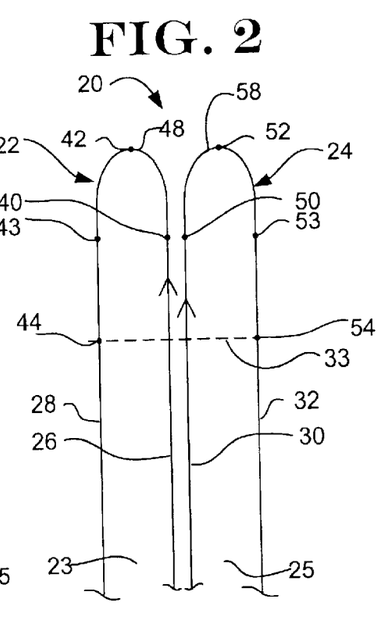
FIG. 2 is a highly diagrammatic, longitudinal, cross-sectional view of the everting membranes of FIG. 1, shown in a more distally advanced position.

FIG. 2 illustrates inner fold 24 and outer fold 22 after the membranes have been everted. In this example, inner fold stationary portion 32 has not moved relative to stationary marker line 33. Similarly, outer fold stationary portion 28 has also not moved with respect to stationary marker line 33. In inner fold 24, advancing portion 30 has been distally advanced relative to stationary marker line 33, thus advancing marker point 50 distally. Distally leading edge 58 now contains marker point 52 which was previously disposed near marker line 33. Outer fold distally leading edge 48 now contains marker point 42 which was also previously disposed near marker line 33. It may be seen from inspection of FIG. 2 that distally advancing membrane portions 26 and 30 cause the respective distally leading edges to advance distally, even though the outermost, stationary portions 28 and 32 remain unmoved. In this way, distally leading edges 58 and 48 are distally advanced by advancing the inner pair of opposed membranes 26 and 30. In one embodiment, opposing membranes 26 and 30 may be coupled at a more proximal location, thus forming inner fold 24 and outer fold 22 out of a single membrane, having a shared interior region.

Figure 3:
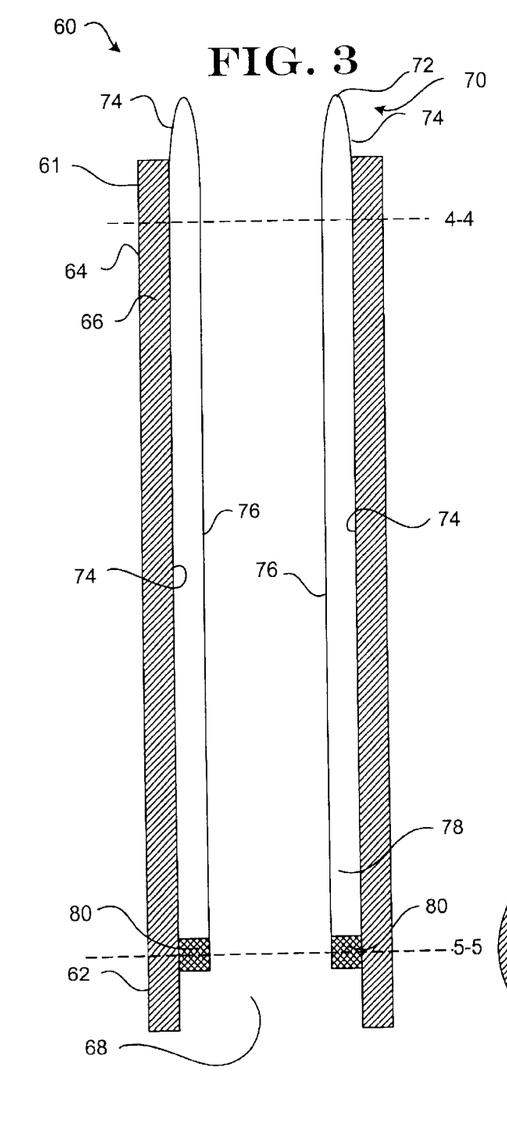
FIG. 3 is a highly diagrammatic, longitudinal, cross-sectional view of a catheter proximal region having a single fold everting membrane.

FIG. 3 illustrates a distal region of a medial device or catheter 60 having a single everting membrane. Catheter 60 includes a tube 64 having a wall 66 and extending between a distal region 61 and a more proximal region 62. Tube 64 includes a central lumen 68 disposed therethrough and having an everting membrane tube 70 disposed within lumen 68. Everting tube 70 includes a non-advancing portion 74 which, in one embodiment, can be fixed relative to tube 64. Everting tube 70 also includes a leading edge 72 and an inner, advancing membrane portion 76. Advancing membrane portion 76 is coupled to an annular sealing ring 80, thereby forming an interior region 78 within everting tube 70. In one embodiment, everting tube 70 has only a relatively short non-advancing portion relative to the advancing portion. In one example of the invention, outer, non-advancing membrane portion 74 begins at about the location denoted by line 4—4 in FIG. 3.

Everting tube interior region 78 may be filled with fluid or gas under pressure which can cause annular sliding seal 80 to move distally, as leading edge 72 is propelled distally forward by the pressure within everting tube 70. The source of the fluid pressure may vary from embodiment to embodiment, with no particular embodiment illustrated in FIG. 3.

Figure 4:
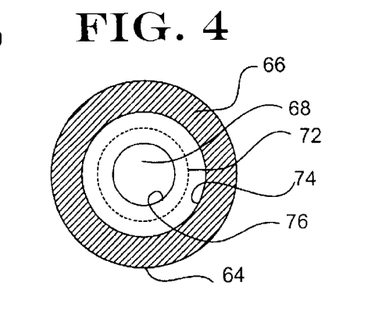
FIG. 4 is a transverse, cross-sectional view taken through line 4—4 of FIG. 3.
Figure 5:
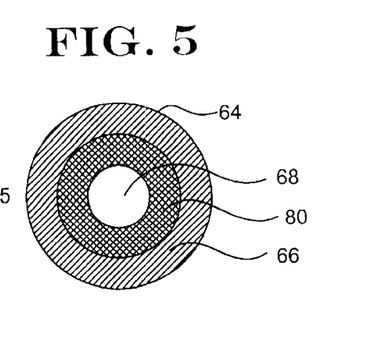
FIG. 5 is a transverse, cross-sectional view taken through line 5—5 of FIG. 3.

Referring now to FIG. 4, tube wall 66 may be seen to be disposed about non-advancing membrane portion 74 and advancing membrane portion 76, having leading edge 72 disposed therebetween. Tube lumen 68 may be seen to be centrally disposed within tube wall 66. FIG. 5 illustrates a more proximal cross-sectional view of device 60, having tube wall 66 disposed about annular sealing ring 80, which is in turn disposed about tube lumen 68. Sealing ring or seal 80, in a preferred embodiment, is free to slide distally and proximally within tube 64.

Figures 6, 7, 8:
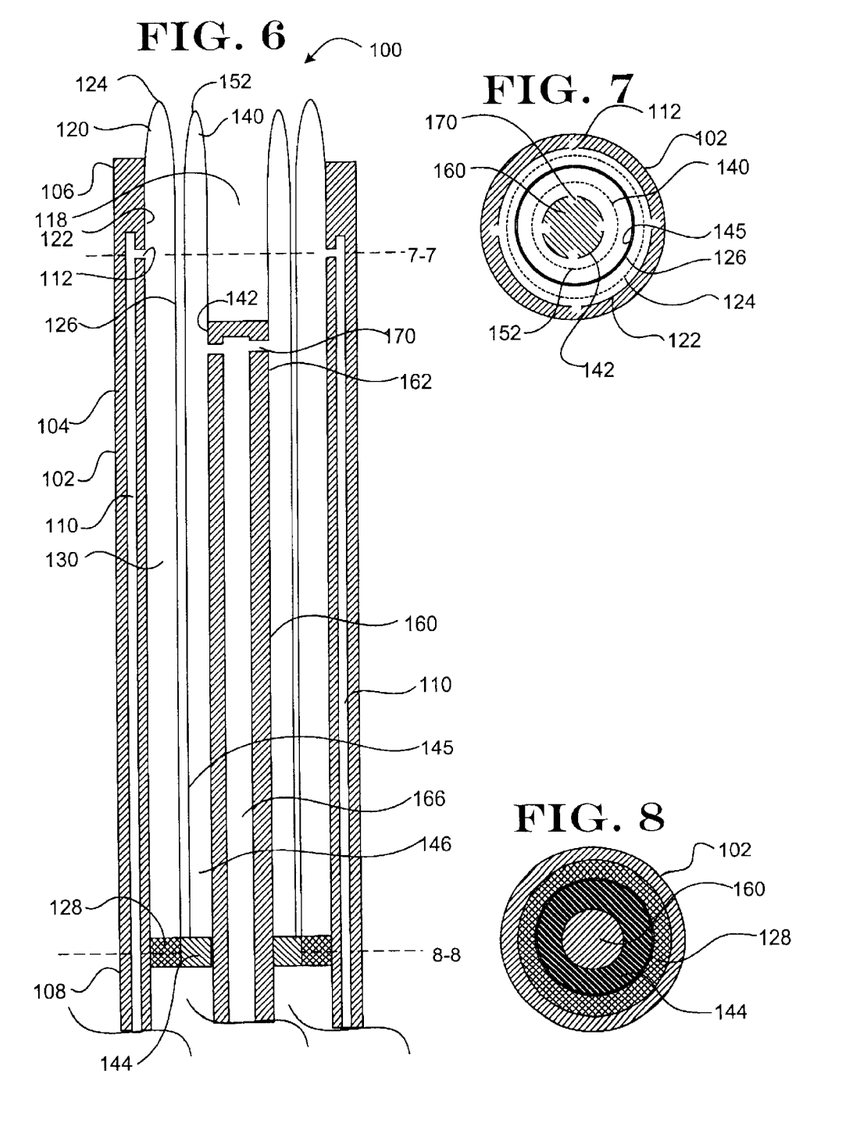
FIG. 6 is a highly diagrammatic, longitudinal, cross-sectional view of a catheter distal region having a two-fold everting membrane.
FIG. 7 is a transverse, cross-sectional view taken through line 7—7 of FIG. 6.
FIG. 8 is a transverse, cross-sectional view taken through line 8—8 of FIG. 6.

FIG. 6 illustrates a distal region of an everting catheter device 100 having a tube 102 disposed about an outer everting membrane 120, disposed about an inner everting membrane 140, disposed in turn about an inner tubular member 160. Tube 102 and device 100 may be seen to have a distal region 106 and a more proximal region 108. Tube 102, in the embodiment illustrated, has a lumen 110 disposed within a tube wall 104. Tube lumen 110 may also be seen to have an orifice 112 that is inwardly directed. Outer everting membrane 120 may be seen to have a fixed or non-advancing portion 122 which can be fixedly secured to the tube wall. Outer everting membrane 120 may also be seen to have a distally leading edge 124 and an advancing membrane portion 126, which is secured to an outer seal 128, which is slidably disposed within tube 102. A second sealing member 144 may be seen to be also disposed within tube 102, having an advancing membrane portion 145, a distally leading edge 152, and a non-advancing or fixed portion 142. Non-advancing portion 142 can be fixedly secured to inner tube 160 as illustrated. Tube 160 may be seen to have a lumen 166 therethrough in fluid communication with an outwardly directed orifice 170. Inner everting membrane 140 may also be seen to have an interior 146. In one embodiment, seals 128 and 144 are one and the same and operate together as a single seal. In another embodiment, the seals slide independent of each other. As may be seen from inspection of FIG. 6, fluid supplied under pressure within tube lumen 110 may flow through orifice 112, into outer everting membrane interior 130, thus propelling outer everting membrane leading edge 124 and seal 128 distally. Similarly, fluids applied under pressure into lumen 166 may be seen to enter inner everting tube interior 146 through orifice 170. The supplied fluid pressure may propel inner membrane leading edge 152 and seal 144 distally. The two everting membranes of FIG. 6 may operate in a manner similar to the everting membranes illustrated in FIGS. 1 and 2.

FIG. 7 illustrates a cross-section taken through line 7—7 of FIG. 6. Outer tube 102 may be seen to enclose non-advancing membrane portion 122, leading edge 124, and advancing membrane portion 126. Inner everting membrane advancing portion 145 may be seen to be disposed about leading edge 152, which is in turn disposed about fixed membrane portion 142. Fixed membrane portion 142 may be seen to fixedly attached to inner tubular member 160. Orifices 112 may be seen to supply the interior of outer everting membrane 120, while orifices 170 may be seen to supply the interior of inner everting membrane 140. The cross-sectional view illustrated in FIG. 7 illustrates some elements, for example, tube 160, shown in projection, that would not be seen in a strict cross-sectional view, but has been added to more clearly illustrate the present invention.

FIG. 8 illustrates a more proximal, transverse cross-sectional view taken through device 100. Outer tube 102 may be seen to be disposed about outer sealing ring 128, which is in turn disposed about inner sealing ring 144, which is slidably disposed on inner tube 160. Inner tube 160 may have a lumen within, not illustrated in FIG. 8. As previously described, outer sealing ring 128 and inner sealing ring 144 are secured to travel together in some embodiments, and allowed to slide separately in other embodiments.

Referring again to FIG. 6, it may be seen that orifices 112 of FIG. 6, illustrated as being disposed on either side of central lumen 110, are not required in some embodiments of the invention. In particular, in one embodiment of the invention, only a portion of tube wall 104 has a lumen 110 therein, and orifice 112 may exist only as a single orifice. In one embodiment where outer everting membrane 120 is a tubular member, it is only necessary to supply the interior of the tubular member at a single orifice in order to distally move outer tube leading edge 124. Similarly, only a single orifice 170 is required to pressurize inner everting membrane 152. In one embodiment of the invention, sealing rings 128 and 144 are tethered or secured to a more proximal, proximally extending member in order to proximally capture the sliding annular rings. In one example, fluid pressure is used to distally advance leading edge 124 and 152 together with sealing rings 128 and 144. In this embodiment, a tethering element, strong in tension but not in compression, may be used to retrieve sealing rings 128 and 144 after the everting membranes have been distally deployed.

Figure 9:
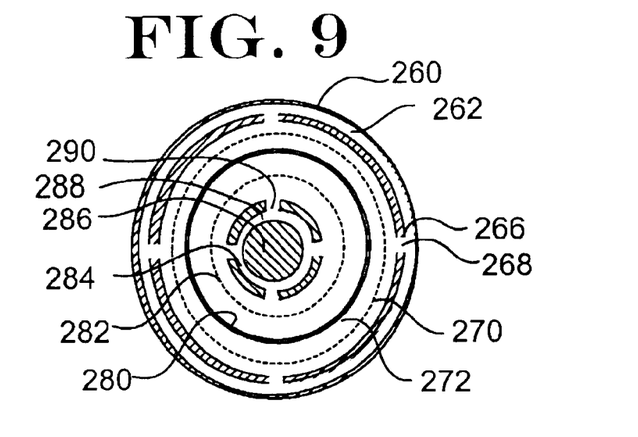
FIG. 9 is a highly diagrammatic, transverse, cross-sectional view of one double everting membrane device having inflation lumens within the inner and outer tubes.

FIG. 9 illustrates one embodiment of the invention having an outer wall 260, a lumen 262, and an inner wall 266, with a plurality of orifices 268 disposed through inner wall 266. Orifices 268 are in fluid communication with the interior of an outer everted membrane, shown having a leading edge 270 and advancing inner membrane portion 272. An inner tube or shaft 286 may be seen to be surrounded by an inner tube lumen 284 in communication with a plurality of orifices 290 which are in fluid communication with the interior of an inner, everted tube having a leading edge 282 and a distally advancing membrane portion 280.

Figure 10:
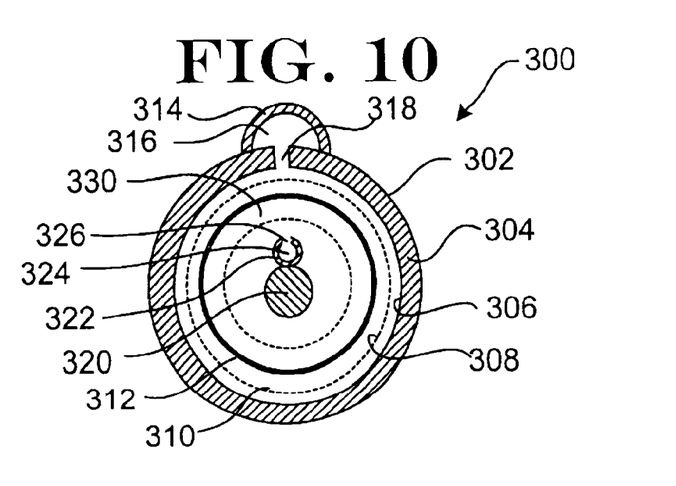
FIG. 10 is a highly diagrammatic, transverse, cross-sectional view of a double everting membrane device having separate inflation tubes for providing fluid pressure.

FIG. 10 illustrates yet another embodiment of the invention, shown in a transverse, cross-sectional view. A tubular everting membrane device 300 may be seen to have an outer tube 302 having a tube wall 304 and an inner wall 306 disposed about an outer everted tube 308 and an inner everted tube 330. Outer everted tube 308 may be seen to have a leading edge 310 and an inner slidably disposed distally advancing edge 312. In the embodiment illustrated, fluid to supply the interior of outer everting tube 310 is supplied by an external tube 314 having a lumen 316 disposed within, and having an orifice 318 supplying outer everting tube 310. Similarly, an inner shaft or tube 320 may be seen to have a separate inflation tube 322 having a lumen 324 in fluid communication with an inflation orifice 326. Inflation orifice 326 may be seen to be in fluid communication with the interior of inner everting tube 330.

Figure 11:
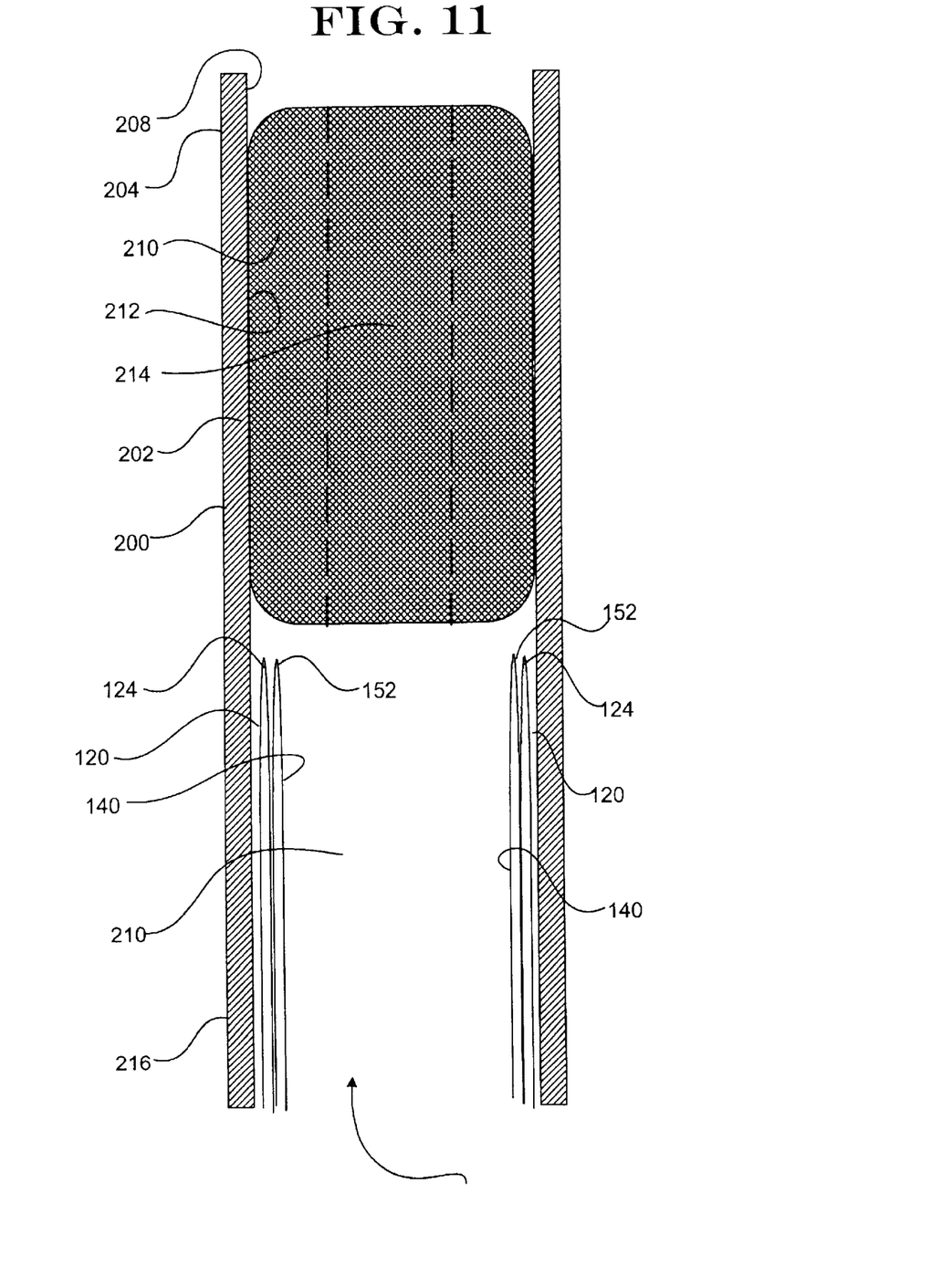
FIG. 11 is a highly diagrammatic, longitudinal, cross-sectional view of a vessel inner wall and plaque, prior to separation by a two-fold everting membrane catheter.

FIG. 11 illustrates a vessel 200, such as a blood vessel, which can be a coronary blood vessel or artery. Vessel 200 includes a vessel wall 202 and a vessel inner wall 208. Vessel 200 has a distal region 204 and a proximal region 206. A plaque deposit 210 is illustrated as at least partially occluding vessel lumen 201. Plaque deposit 210 has an outer portion or surface 212 which is disposed against vessel inner wall 208. In the embodiment illustrated, plaque 210 has at least partial patency, having a lumen 214 therethrough. Double everting membrane device 100 of FIG. 6 may be seen to be disposed proximal of plaque deposit 210. In FIG. 11, outer everting tube leading edge 124 and inner everting tube leading edge 152 are disposed proximally of plaque deposit 210.

Figure 12:
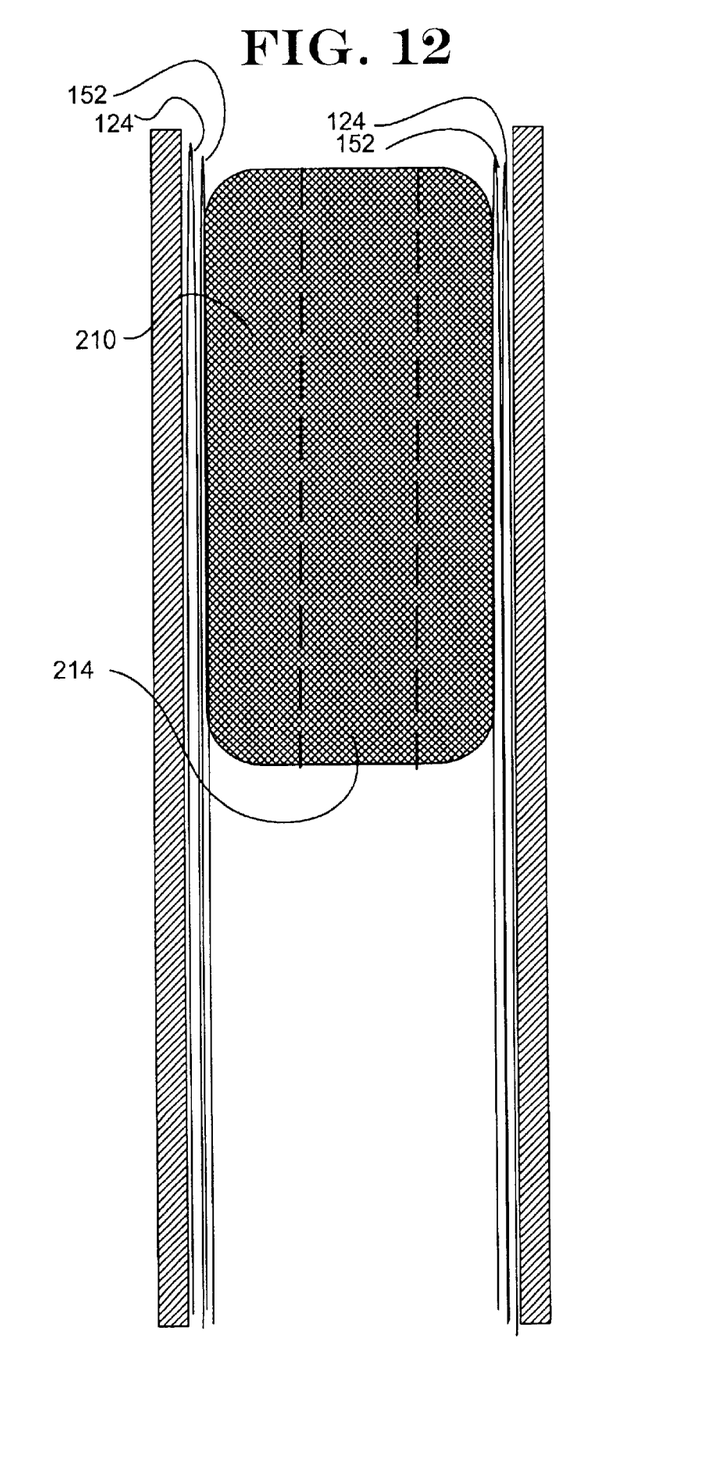
FIG. 12 is a highly diagrammatic, longitudinal, cross-sectional view of the vessel of FIG. 11, after distal advancement of the everting membranes of FIG. 11.

FIG. 12 illustrates double everting membrane device 100, after outer everting membrane 120 and inner everting membrane 140 have been distally advanced past plaque deposit 210. As may be seen from inspection of FIG. 12, outer tube distally leading edge 124 and inner tube distally leading edge 152 have been distally advanced past plaque deposit 210. The two everting membranes have been used to separate plaque deposit 210 from vessel wall or walls 202. With the everting membranes thus advanced distally beyond plaque deposit 210, the plaque deposit may be removed from within the vessel. In one embodiment, everting membranes 120 and 140 may be distally advanced even further, to more completely engulf plaque deposit 210. In one use of the present invention, inner tube 140 and outer tube 120 may be distally retracted, while containing plaque deposit 210 within.

In one method according to the present invention, a guidewire is initially advanced through vessel lumen 201 and through plaque lumen 214. After a guidewire has been disposed distally of plaque 210, an emboli-capturing mechanism such as a distal occlusion filter may be distally advanced over the positioned guidewire. The distal occlusion device may be used to capture any small portion of plaque deposit 210 which became free in the blood stream as a result of the process. After plaque deposit 210 has been separated from wall 202, both the emboli filter and plaque deposit may be proximally retracted from within the vessel. In one method according to the present invention, device 100 may be advanced distally through the vasculature from an entry point near the groin in the femoral artery. In a preferred use of the present invention, vessel 200 is a coronary artery.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A method for separating plaque from a blood vessel, said blood vessel having an inner wall, said plaque having a body portion, said plaque being disposed along at least part of said vessel inner wall, the method comprising:

providing an everting membrane;

intravascularly inserting said everting membrane to near said plaque;

everting said membrane into a distally advancing portion, a distally leading edge, and a non-advancing portion, such that said distally advancing portion is distally advancing into said vessel, such that said leading edge is distally advancing into said vessel; and advancing said advancing membrane portion and leading edge into said vessel along said vessel inner wall, such that said plaque is separated from said vessel inner wall.

2. A method for separating plaque from a blood vessel, the blood vessel having an inner wall, said plaque having a body portion, said plaque being disposed along at least part of said vessel inner wall, the method comprising:

providing an outer everting membrane tube having an outer tube distally leading edge;

providing an inner everting membrane tube having an outer tube distally leading edge, wherein said inner tube is disposed within said outer tube;

intravascularly inserting said inner and outer everting membrane tubes to near said plaque; and distally advancing said inner and outer everting membrane tubes between said plaque body and said vessel inner wall by everting said inner and outer membrane tubes, such that said plaque is separated from said vessel inner wall.

3. A method for separating plaque from a blood vessel inner wall, said plaque having a body portion, said plaque being disposed along at least part of said vessel inner wall, the method comprising:

providing a membrane including an inner fold and an outer fold;

wherein said inner fold includes an inner fold inner portion, an inner fold outer portion and an inner fold distally leading edge disposed between said inner fold inner and outer portions;

wherein said outer fold includes an outer fold inner portion, an outer fold outer portion and an outer fold distally leading edge disposed between said outer fold inner and outer portions;

distally advancing said inner fold outer portion such that said inner fold leading edge is made to distally advance in between said plaque and said vessel wall; and distally advancing said outer fold inner portion such that said outer fold leading edge is made to distally advance in between said plaque and said vessel wall.

4. A method for separating plaque from a blood vessel as in claim 3, wherein, during said distally advancing steps, said outer fold outer portion is maintained substantially immobile with respect to said vessel inner wall, wherein said inner fold inner portion is maintained substantially immobile with respect to said plaque.

5. A method for separating plaque from a blood vessel as in claim 3, wherein only one of said inner and outer folds are actively distally advanced, wherein the non-actively advanced fold is effectively distally moved by the actively advanced fold.

6. A method for separating plaque from a blood vessel as in claim 3, wherein said inner and outer folds are joined together at a location proximal of said outer fold inner portion and said outer fold outer portion.

7. A method for separating plaque from a blood vessel as in claim 3, wherein said inner and outer folds each have interior portions disposed within said inner and outer portions, wherein said inner and outer fold distally advancing step includes introducing fluid under pressure into at least one of said inner fold interior portion and outer fold interior portion.

8. A method for separating plaque from a blood vessel as in claim 3, wherein said inner and outer folds each have interior portions disposed within said inner and outer portions, wherein said inner and outer fold distally advancing steps include introducing fluid under pressure into said inner fold interior and said outer fold interior.

9. A method for separating plaque from a vessel inner wall comprising everting at least two membranes in between said plaque and said vessel inner wall.

10. A method for separating plaque from a vessel inner wall as in claim 9, further comprising intravascularly inserting said at least two membranes to a location near said plaque prior to said everting step.

11. An intravascular device for separating plaque from a vessel inner wall, the device comprising:

a tubular member having a distal region and an inflation lumen;

a flexible membrane including an inner fold and an outer fold, each fold having an interior and a distally leading edge;

said membrane inner fold having a proximal, distally advancing portion;

said membrane outer fold having a proximal, distally advancing portion, wherein said membrane inner and outer proximal distally advancing portions are coupled together; and said inner fold and outer fold interiors being in fluid communication with said tube inflation lumen, such that supplying fluid under pressure to said inflation lumen causes said inner and outer fold distally leading edges to travel distally.

* * * * *